(12) United States Patent
Shekalim

(10) Patent No.: US 12,053,621 B2
(45) Date of Patent: *Aug. 6, 2024

(54) COVER FOR LIQUID DELIVERY SYSTEM WITH INTEGRATED PLUNGER POSITION SENSING, AND CORRESPONDING METHOD

(71) Applicant: Patients Pending Ltd., London (GB)

(72) Inventor: Avraham Shekalim, Nesher (IL)

(73) Assignee: PATIENTS PENDING LTD., London (GB)

( * ) Notice: Subject to any disclaimer, the term of this patent is extended or adjusted under 35 U.S.C. 154(b) by 471 days.

This patent is subject to a terminal disclaimer.

(21) Appl. No.: 16/919,743

(22) Filed: Jul. 2, 2020

(65) Prior Publication Data
US 2020/0330691 A1 Oct. 22, 2020

Related U.S. Application Data

(63) Continuation of application No. 15/743,169, filed as application No. PCT/IB2016/053374 on Jun. 8, 2016, now Pat. No. 10,702,658.
(Continued)

(51) Int. Cl.
*A61M 5/315* (2006.01)
*A61M 5/31* (2006.01)
(Continued)

(52) U.S. Cl.
CPC .......... *A61M 5/31525* (2013.01); *G01D 5/26* (2013.01); *G01F 11/006* (2013.01);
(Continued)

(58) Field of Classification Search
CPC ...... A61M 5/31525; A61M 2005/3126; A61M 2205/3306; A61M 2205/332;
(Continued)

(56) References Cited

U.S. PATENT DOCUMENTS 5,233,571 A 8/1993 Wirtschafter
5,282,793 A 2/1994 Larson
(Continued)

FOREIGN PATENT DOCUMENTS

EP 2879740 3/2017
JP 2001-170176 6/2001
(Continued)

OTHER PUBLICATIONS

Extended European Search Report in European Application No. 16823948.1, dated Jun. 6, 2018.
(Continued)

*Primary Examiner* — Bradley J Osinski
(74) *Attorney, Agent, or Firm* — HSML P.C.

(57) ABSTRACT

A sliding cover for a liquid delivery device, such as a cap (100) for a pen injector (200), incorporates a set of sensors including a first optical sensor (110) with an output which changes during uncapping or capping motions on passing of a plunger (220) of the pen injector. This output is used together with at least one additional sensor output to determine the position of the plunger along a cylinder (210) of the liquid delivery device. By monitoring changes in the plunger position, the quantity of dosages delivered by the liquid delivery device can be determined, displayed, stored and/or transmitted to an external device for further data processing or storage.

24 Claims, 13 Drawing Sheets

Related U.S. Application Data

(60) Provisional application No. 62/325,470, filed on Apr. 21, 2016, provisional application No. 62/191,411, filed on Jul. 12, 2015.

(51) Int. Cl.
*G01D 5/26* (2006.01)
*G01F 11/00* (2006.01)
*G01F 11/02* (2006.01)

(52) U.S. Cl.
CPC ... *G01F 11/029* (2013.01); *A61M 2005/3126* (2013.01); *A61M 2205/3306* (2013.01); *A61M 2205/332* (2013.01); *A61M 2205/3327* (2013.01); *A61M 2205/3379* (2013.01); *A61M 2205/35* (2013.01); *A61M 2205/502* (2013.01)

(58) Field of Classification Search
CPC .. A61M 2205/3327; A61M 2205/3379; G01D 5/26; G01F 11/029
See application file for complete search history.

(56) References Cited

U.S. PATENT DOCUMENTS

| | | | |
|---|---|---|---|
| 5,523,560 A | 6/1996 | Manique et al. | |
| 5,564,414 A | 10/1996 | Walker et al. | |
| 5,645,534 A | 7/1997 | Chanoch | |
| 6,113,578 A | 9/2000 | Brown | |
| 6,270,455 B1 | 8/2001 | Brown | |
| 6,277,099 B1 | 8/2001 | Strowe et al. | |
| 6,287,283 B1 | 9/2001 | Ljunggreen et al. | |
| 6,452,158 B1 | 9/2002 | Whatley et al. | |
| 6,482,185 B1 | 11/2002 | Hartmann | |
| 6,585,698 B1 * | 7/2003 | Packman | G16H 20/17 604/207 |
| 6,685,678 B2 | 2/2004 | Evans et al. | |
| 6,707,763 B2 | 3/2004 | Osberg et al. | |
| 6,845,064 B2 | 1/2005 | Hildebrandt | |
| 7,133,329 B2 | 11/2006 | Skyggebjerg et al. | |
| 7,138,906 B2 | 11/2006 | Rosche | |
| 7,362,660 B2 | 4/2008 | Hildebrandt | |
| 7,397,730 B2 | 7/2008 | Skyggebjerg et al. | |
| 7,498,563 B2 | 3/2009 | Mandro et al. | |
| 7,499,581 B2 | 3/2009 | Tribble et al. | |
| 7,713,229 B2 | 5/2010 | Veit et al. | |
| 8,052,655 B2 | 11/2011 | Moller et al. | |
| 8,057,441 B2 | 11/2011 | Tsubota | |
| 8,083,711 B2 | 12/2011 | Enggaard | |
| 8,197,449 B2 | 6/2012 | Nielsen et al. | |
| 8,221,356 B2 | 7/2012 | Enggaard | |
| 8,221,359 B2 | 7/2012 | Kristensen et al. | |
| 8,348,904 B2 | 1/2013 | Peterson | |
| 8,551,039 B2 | 10/2013 | Veit et al. | |
| 8,556,867 B2 | 10/2013 | Krulevitch et al. | |
| 8,560,271 B2 | 10/2013 | Koehler et al. | |
| 8,632,509 B2 | 1/2014 | Moller et al. | |
| 8,743,662 B2 | 6/2014 | Sjolund et al. | |
| 8,758,322 B2 | 6/2014 | McCoy et al. | |
| 8,773,660 B2 | 7/2014 | Pommereau et al. | |
| 8,817,258 B2 | 8/2014 | Whatley et al. | |
| 8,821,452 B2 | 9/2014 | Dasbach et al. | |
| 8,932,250 B2 | 1/2015 | Montgomery et al. | |
| 9,078,973 B2 | 7/2015 | Harms et al. | |
| 9,078,983 B2 | 7/2015 | Herr | |
| 9,089,650 B2 | 7/2015 | Nielsen et al. | |
| 9,108,006 B2 | 8/2015 | Jensen et al. | |
| 9,125,991 B2 | 9/2015 | Schabbach et al. | |
| 9,205,193 B2 | 12/2015 | Boesen | |
| 9,250,111 B2 | 2/2016 | Whalley et al. | |
| 9,255,830 B2 | 2/2016 | Whalley et al. | |
| 9,272,094 B2 | 3/2016 | Boyd et al. | |
| 9,345,839 B2 | 5/2016 | Shetty et al. | |
| 9,435,666 B2 | 9/2016 | Richter | |
| 9,452,108 B2 | 9/2016 | Ariagno et al. | |
| 9,457,147 B2 | 10/2016 | Green | |
| 9,514,131 B1 | 12/2016 | Bochenko et al. | |
| 9,566,390 B2 | 2/2017 | Boyd et al. | |
| 2003/0133372 A1 | 7/2003 | Fasen et al. | |
| 2003/0161744 A1 | 8/2003 | Vilks et al. | |
| 2004/0062148 A1 | 4/2004 | Skyggebjerg et al. | |
| 2004/0135078 A1 | 7/2004 | Mandro et al. | |
| 2004/0207385 A1 | 10/2004 | Gafner et al. | |
| 2005/0171476 A1 | 8/2005 | Judson et al. | |
| 2006/0139151 A1 | 6/2006 | Rosche | |
| 2006/0178578 A1 | 8/2006 | Tribble et al. | |
| 2007/0203458 A1 | 8/2007 | Tsubota | |
| 2008/0312584 A1 | 12/2008 | Montgomery et al. | |
| 2009/0131875 A1 | 5/2009 | Green | |
| 2009/0299279 A1 | 12/2009 | Richter | |
| 2009/0318865 A1 | 12/2009 | Moller et al. | |
| 2010/0106098 A1 | 4/2010 | Atterbury et al. | |
| 2010/0324728 A1 | 12/2010 | Rosenblum | |
| 2011/0023281 A1 | 2/2011 | Schraga | |
| 2011/0184343 A1 | 7/2011 | Veit et al. | |
| 2011/0264033 A1 | 10/2011 | Jensen et al. | |
| 2011/0295215 A1 | 12/2011 | Nielsen et al. | |
| 2011/0313395 A1 | 12/2011 | Krulevitch et al. | |
| 2012/0078194 A1 | 3/2012 | Moller et al. | |
| 2012/0123347 A1 | 5/2012 | Boyd et al. | |
| 2012/0165746 A1 | 6/2012 | Harms et al. | |
| 2013/0310756 A1 * | 11/2013 | Whalley | A61M 5/31 604/189 |
| 2014/0014733 A1 | 1/2014 | Kato | |
| 2014/0209603 A1 | 7/2014 | Aneas | |
| 2015/0018770 A1 | 1/2015 | Baran et al. | |
| 2015/0018775 A1 | 1/2015 | Groeschke et al. | |
| 2015/0025502 A1 | 1/2015 | Spenser et al. | |
| 2015/0053711 A1 | 2/2015 | Ariagno et al. | |
| 2015/0246179 A1 | 9/2015 | Zur et al. | |
| 2016/0012205 A1 | 1/2016 | Saint et al. | |
| 2016/0030673 A1 | 2/2016 | White et al. | |
| 2016/0047743 A1 | 2/2016 | Blei et al. | |
| 2016/0074587 A1 | 3/2016 | Searle et al. | |
| 2016/0213848 A1 | 7/2016 | Whalley et al. | |
| 2016/0223380 A1 | 8/2016 | Whalley et al. | |
| 2016/0271336 A1 | 9/2016 | Thomsen | |
| 2017/0312445 A1 | 11/2017 | Mirov et al. | |
| 2018/0078711 A1 | 3/2018 | Krasnow et al. | |
| 2018/0113993 A1 | 4/2018 | Wiser et al. | |

FOREIGN PATENT DOCUMENTS

| | | |
|---|---|---|
| JP | 2009-050709 | 3/2009 |
| JP | 2013-505433 | 2/2013 |
| JP | 2015-518747 | 7/2015 |
| WO | 1998/03215 | 1/1998 |
| WO | 2011032960 | 3/2011 |
| WO | 2013/177135 | 11/2013 |

OTHER PUBLICATIONS

PCT International Search Report and Written Opinion in International Application. No. PCT/IB2016/053374, dated Oct. 4, 2016, 10 pages.
PCT International Preliminary Report on Patentability in International Application No. PCT/IB2016/053374, dated Jan. 25, 2018, 10 pages.
Office Action issued for Japanese Patent Application No. 2021-120094, Jun. 13, 2022, 8 pages including English translation.
Office Action issued for Japanese Patent Application No. 2018-502158, mailed on Aug. 5, 2020, 7 pages including English translation.

* cited by examiner

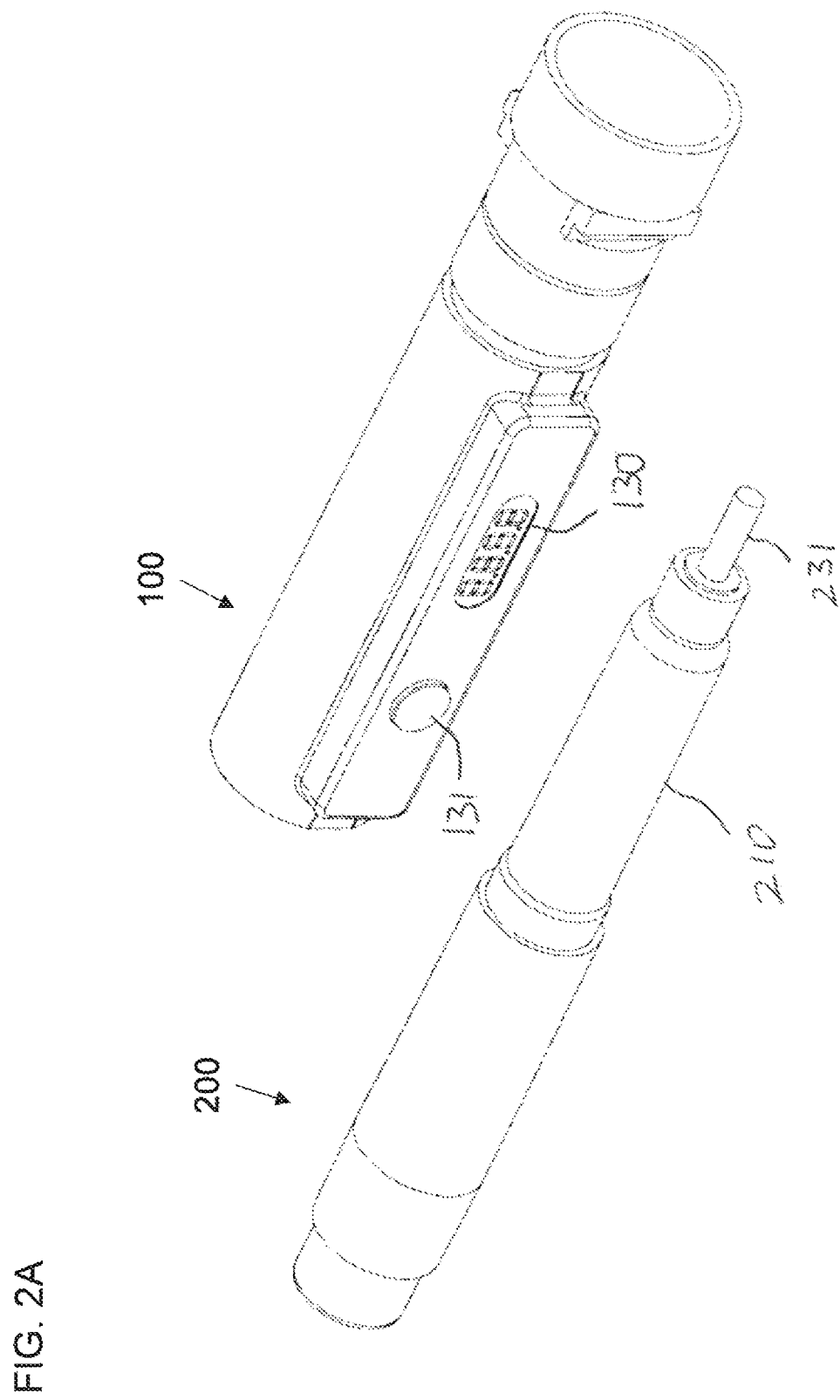

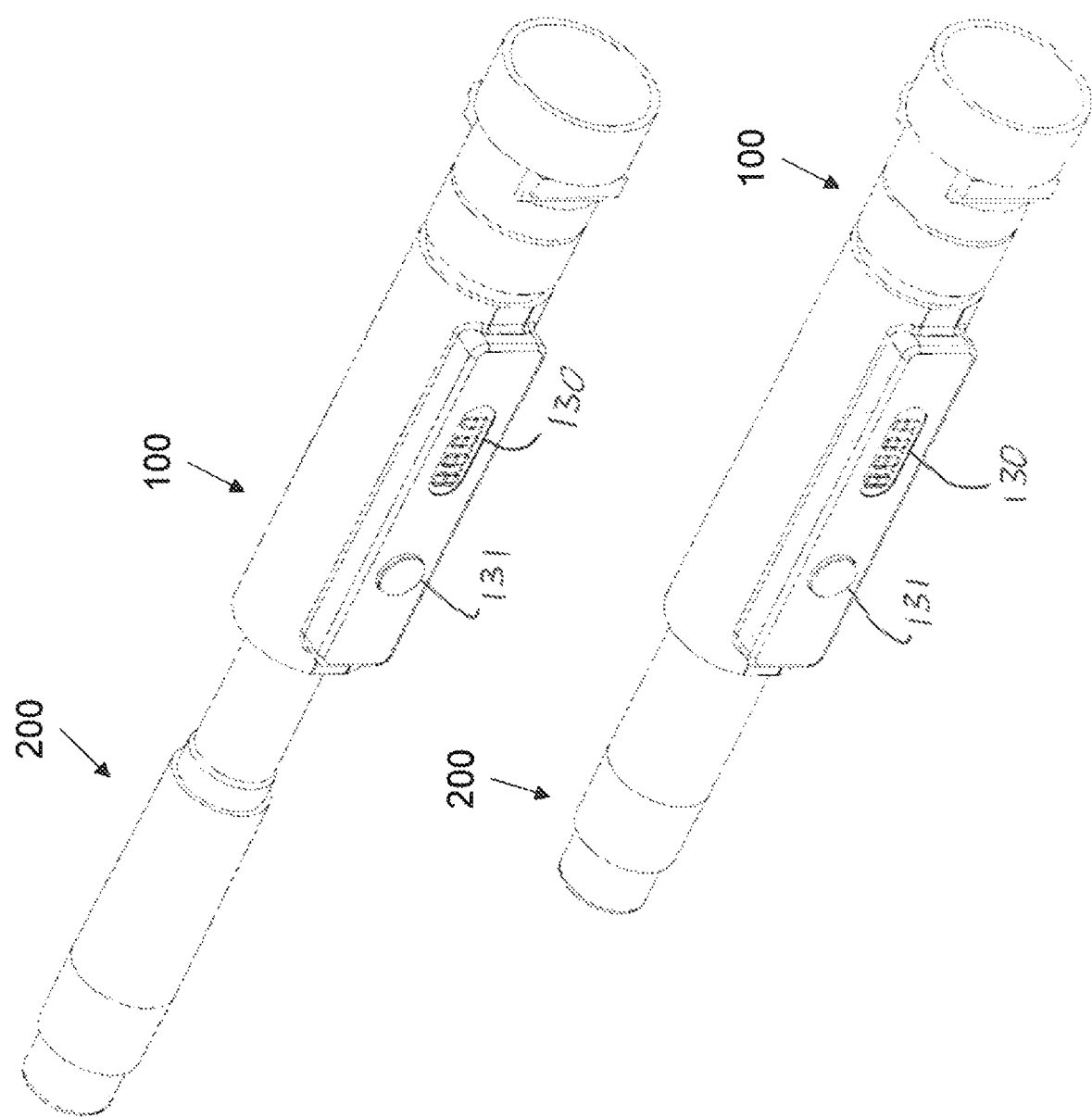

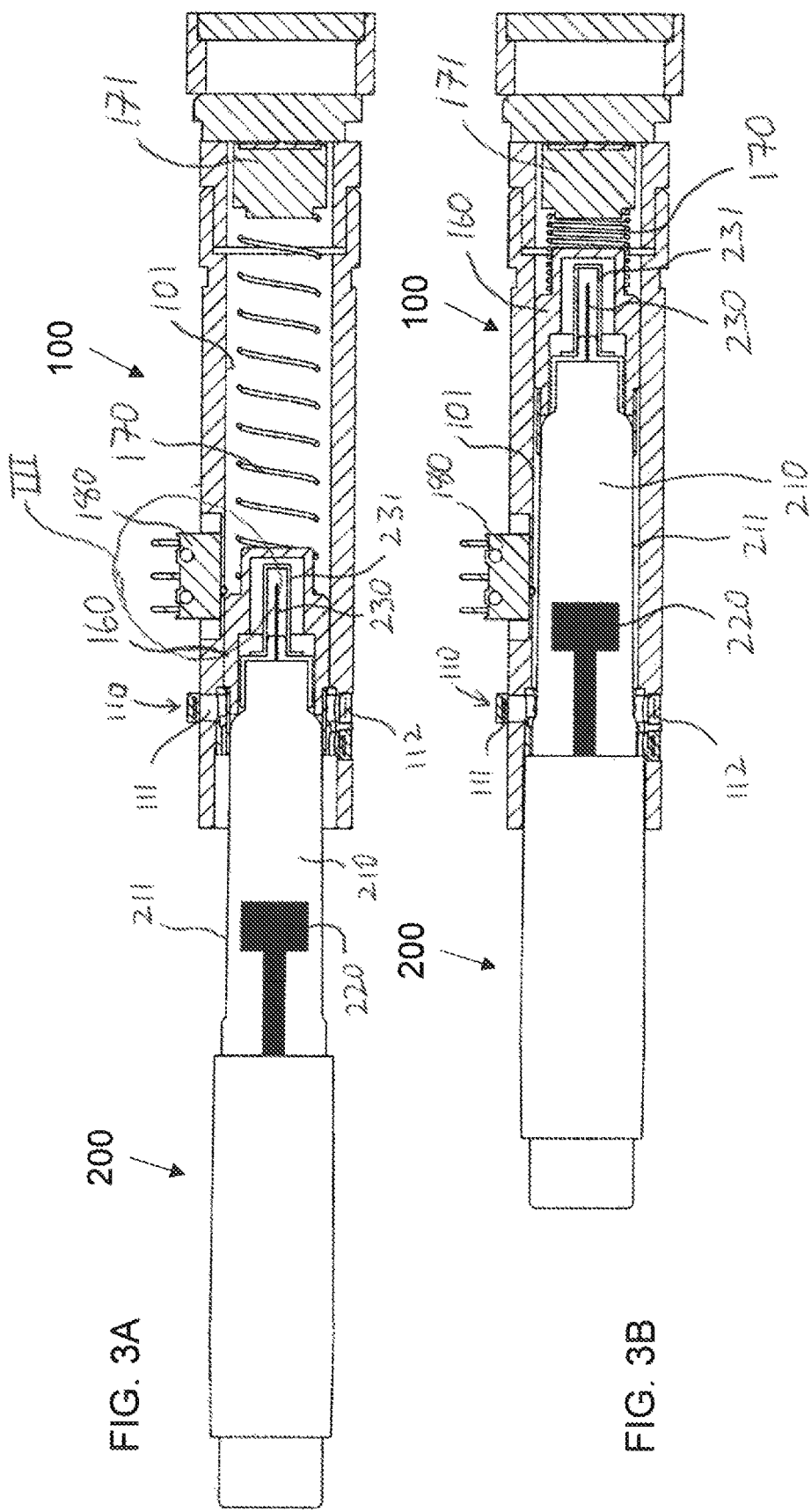

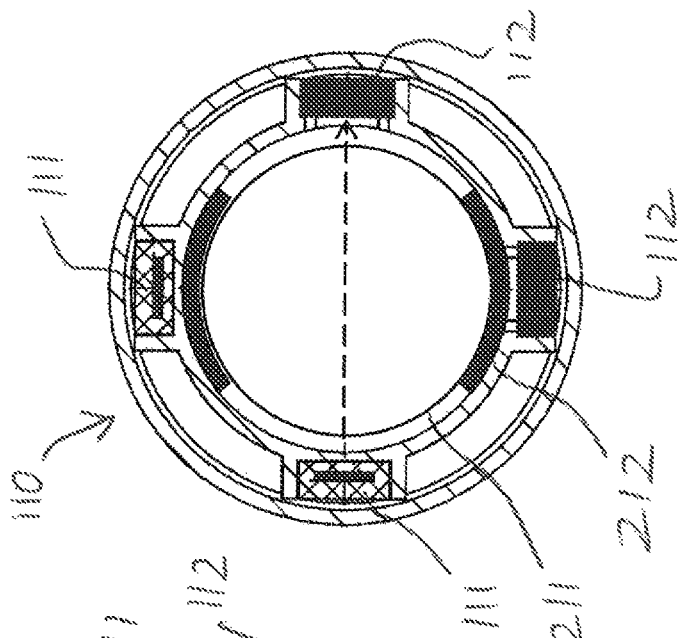
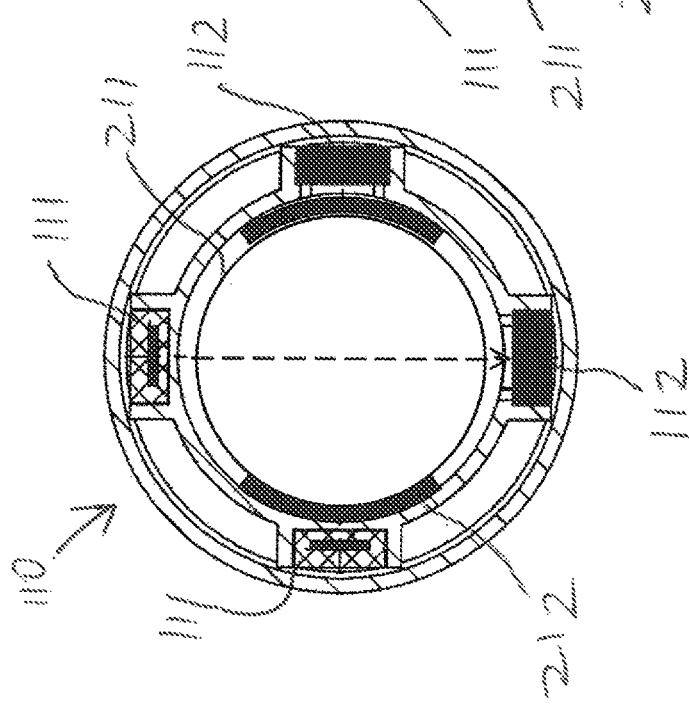
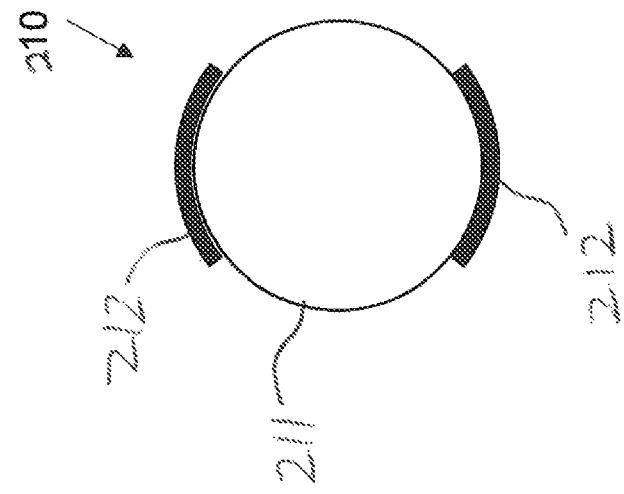

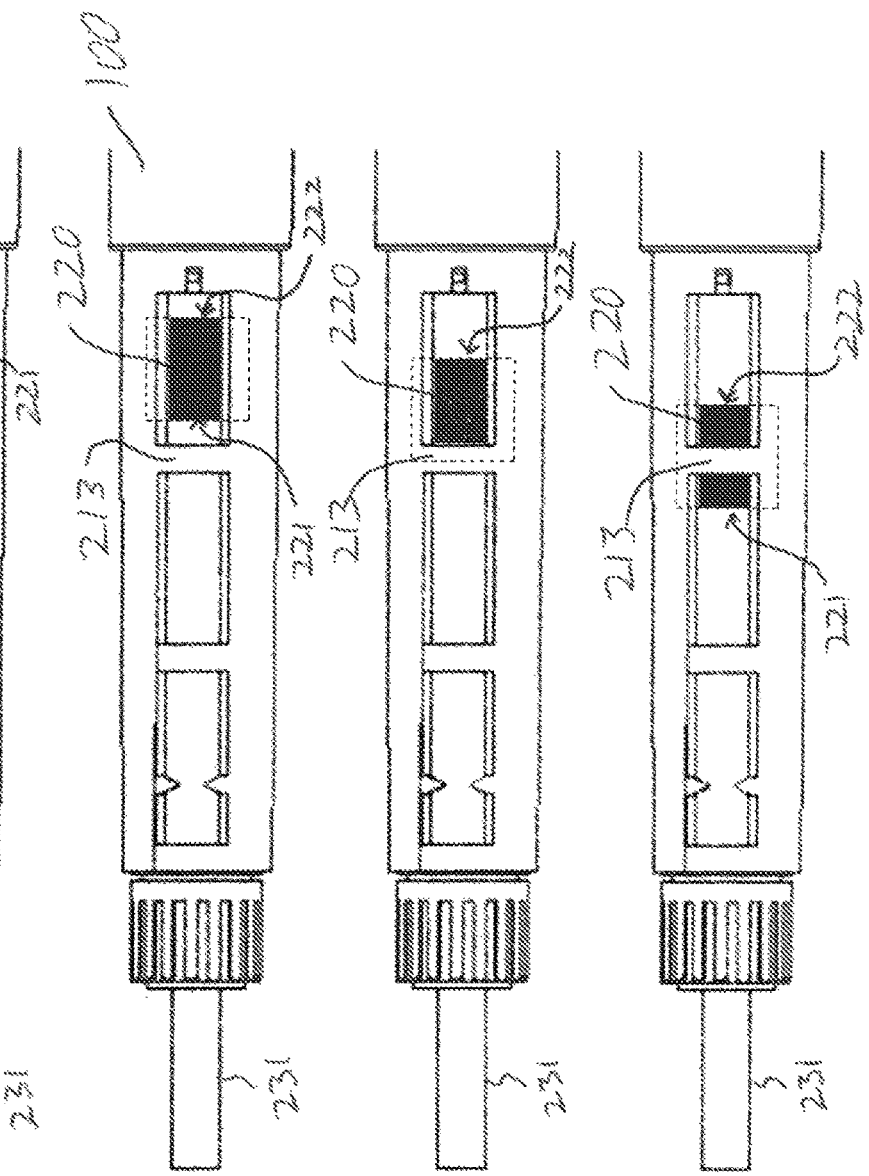

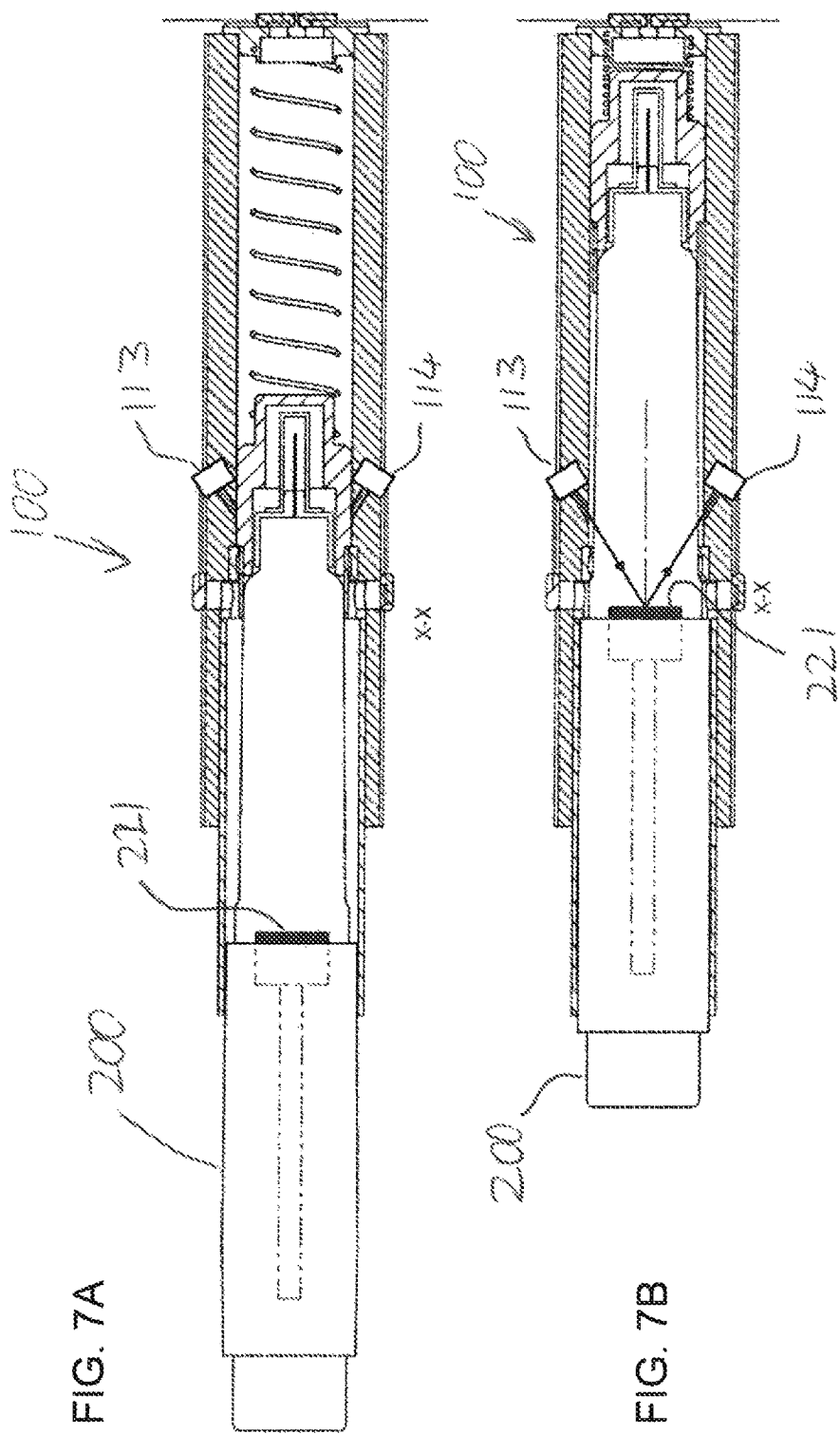

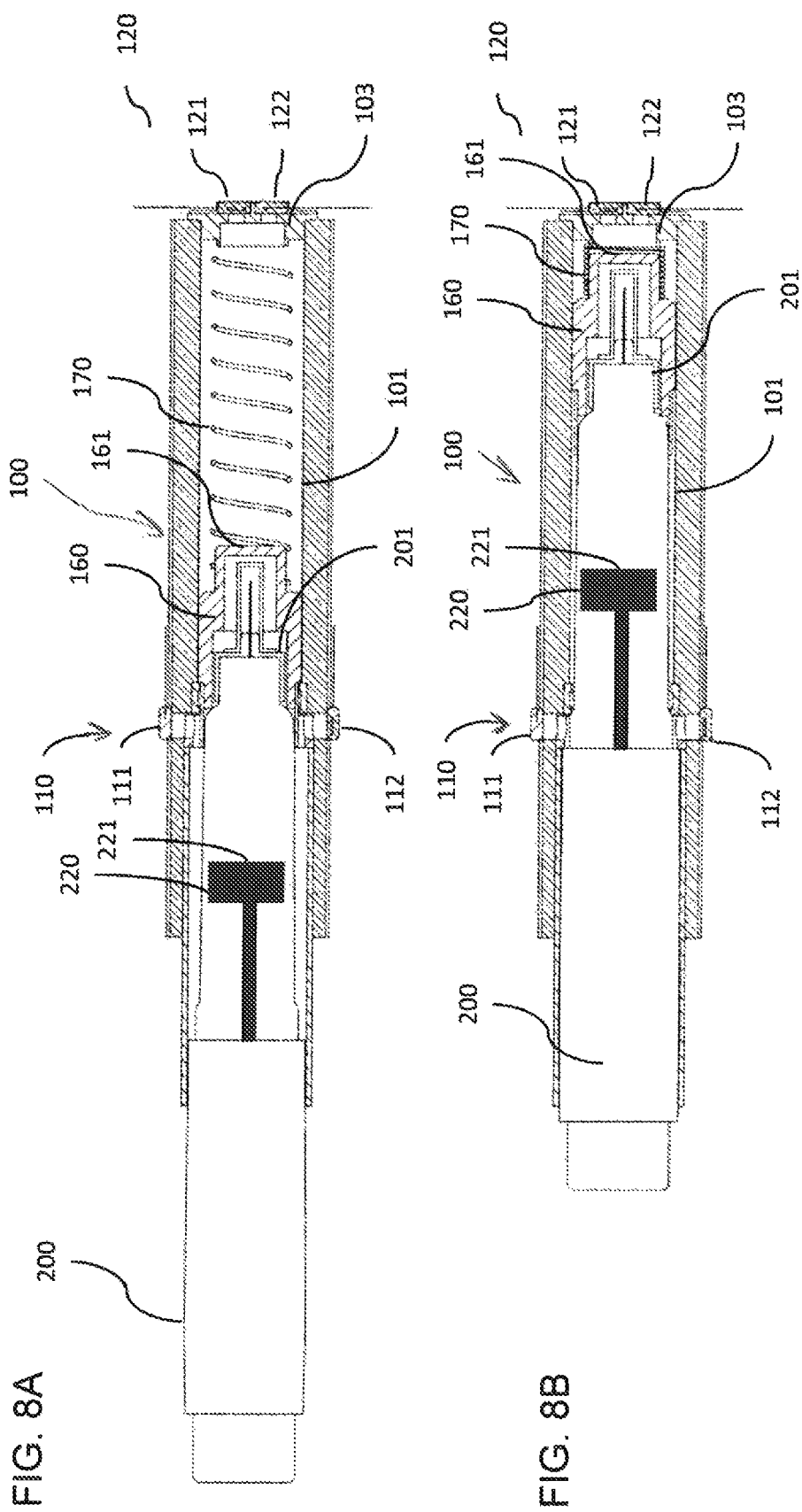

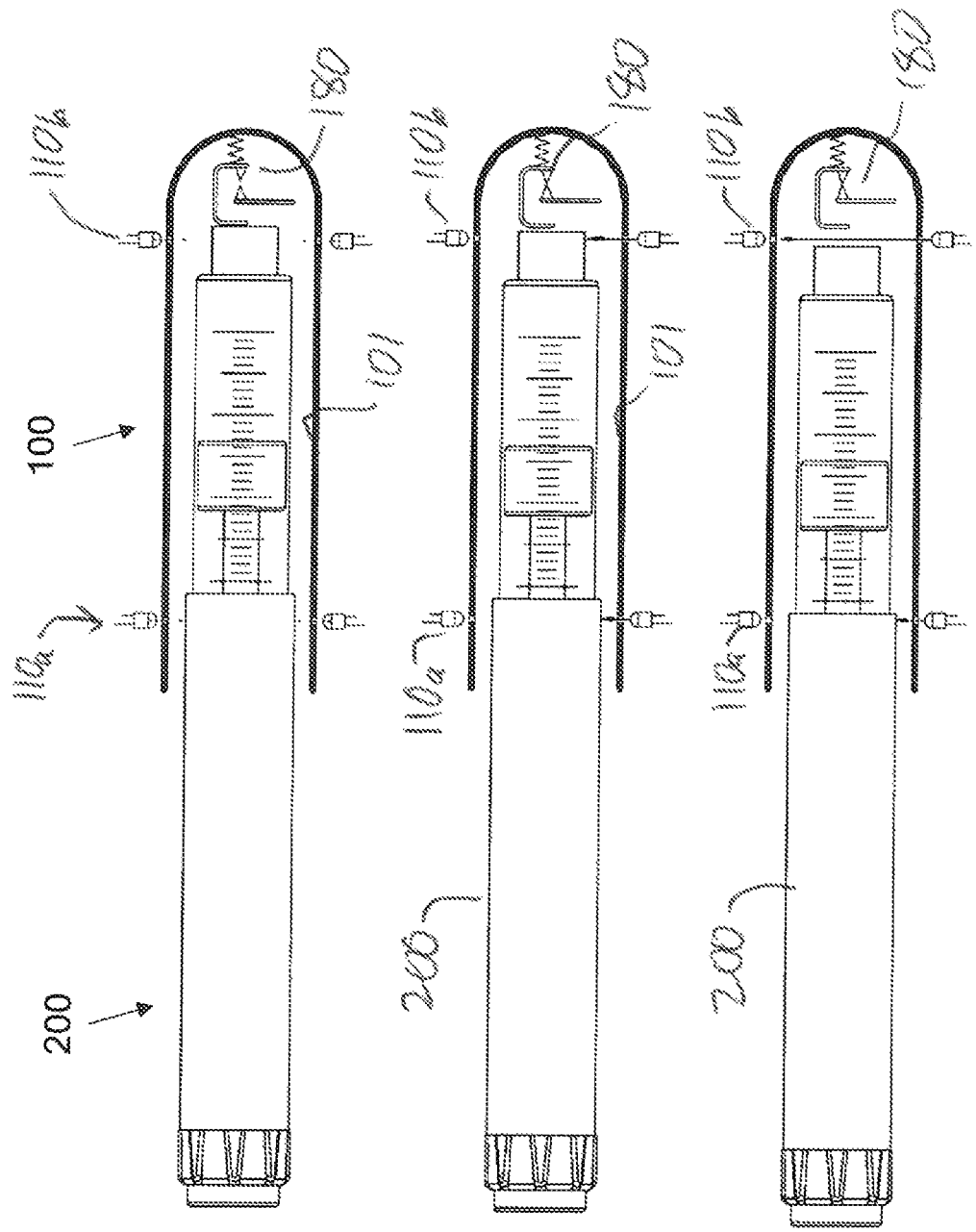

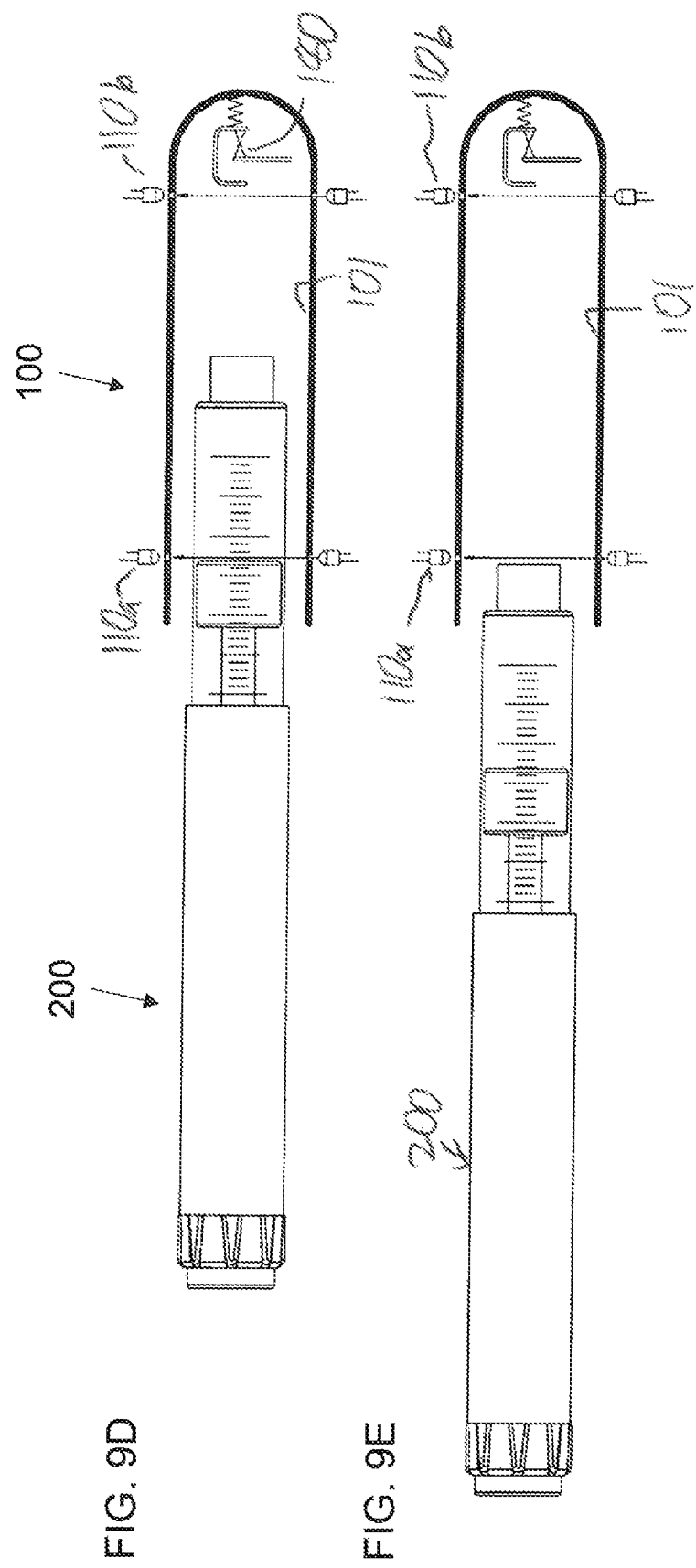

COVER FOR LIQUID DELIVERY SYSTEM WITH INTEGRATED PLUNGER POSITION SENSING, AND CORRESPONDING METHOD

FIELD AND BACKGROUND OF THE INVENTION

The present invention relates to liquid delivery systems and, in particular, it concerns an apparatus and method for measuring the timing and quantity of doses delivered by a pen-injector type drug delivery device and/or monitoring the quantity of drug remaining in the device.

In the field of liquid delivery devices, and particularly pen injectors, there is a need to provide the user with reliable information regarding previously administered doses of a liquid drug.

Various attempts have been made to add functionality to pen injectors by providing a smart cap. By way of example, U.S. Pat. No. 8,743,662, coassigned with the present invention, discloses a smart cap for a pen injector which monitors the time which has elapsed since a previous use of the pen injector.

Other smart cap devices have attempted to measure the quantity of a drug dose dispensed. One example of such a device is U.S. Pat. No. 8,817,258. This device requires an extensive array of optical sensors extending along the cap.

SUMMARY OF THE INVENTION

The present invention is an apparatus in which sensors are integrated with a sliding cover of a liquid delivery system, and measure the position of a plunger of the liquid delivery system while the cover is being removed or replaced.

According to the teachings of an embodiment of the present invention there is provided, an apparatus for use with a liquid delivery system, the liquid delivery system including a transparent cylinder for housing a liquid and an at least partially opaque plunger movable along an axis of the cylinder for expelling the liquid through an outlet, the apparatus comprising: (a) a sliding cover configured for sliding engagement with the cylinder so as to be slidable along the cylinder parallel to the axis from a first position to a second position; (b) a set of sensors housed in the sliding cover so as to move together with the sliding cover, the set of sensors comprising: (i) an optical sensor having an optical emitter for emitting radiation and an optical receiver for generating a first output indicative of an amount of the radiation received by the optical receiver, the optical sensor being deployed in inward-facing deployment such that, when the sliding cover slides in engagement with the transparent cylinder, the first output changes as the optical sensor passes the plunger, and (ii) a position sensor deployed for generating a second output indicative of a current position of the sliding cover between the first position and the second position; and (c) a processing system associated with the set of sensors so as to receive at least the first output and the second output, the processing system being configured to be responsive to a variation in the first output indicative of the optical sensor reaching the plunger to determine a corresponding current position of the sliding cover as indicated by the second output, and thereby to determine a location of the plunger along the cylinder.

According to a further feature of an embodiment of the present invention, the sliding cover is implemented as a cap with a central bore for receiving an end portion of a pen injector having a projecting needle.

According to a further feature of an embodiment of the present invention, the optical sensor is implemented using a plurality of the optical emitters spaced around the central bore and a corresponding plurality of optical receivers spaced around the central bore, such that, when used with a pen injector having optical obstructions extending along the transparent cylinder parallel to the axis, at least one pair of optical emitter and optical receiver are unobstructed.

According to a further feature of an embodiment of the present invention for a pen injector having a number of fixed optical obstructions spaced along the transparent cylinder, the processing system is configured: (a) to process the first output to detect variations indicative of the first optical sensor passing a front edge of the plunger and a rear edge of the plunger; (b) to determine a location of the front edge of the plunger along the cylinder; and (c) on detecting that a front edge of the plunger is approaching a fixed optical obstruction, to determine a location of the rear edge of the plunger.

According to a further feature of an embodiment of the present invention for use with a pen injector having an initial plunger position recessed within an opaque housing, the set of sensors further comprises a supplementary optical sensor having an optical emitter for emitting radiation at an oblique angle through a wall of the transparent cylinder towards a surface of the plunger and an optical receiver for generating a supplementary output indicative of an amount of the obliquely angled radiation received by the optical receiver.

According to a further feature of an embodiment of the present invention, there is also provided a cradle slidingly mounted within the central bore, the cradle configured for receiving the end portion of the pen injector, the cradle being spring biased towards an end position for engaging the end portion of the pen injector when the sliding cover is in the first position, and being retractable to move together with the end portion of the pen injector as the sliding cover slides to the second position.

According to a further feature of an embodiment of the present invention, the position sensor is associated with the cradle so that the second output is indicative of a current position of the cradle within the central bore.

According to a further feature of an embodiment of the present invention, there is also provided a cradle spring deployed for biasing the cradle towards the end position, and wherein the position sensor includes a load cell deployed for measuring a compression force in the cradle spring.

According to a further feature of an embodiment of the present invention, there is also provided a force adjustment spring deployed within the sliding cover such that a biasing force acting on the cradle corresponds to a combination of the forces from the cradle spring and from the force adjustment spring, and wherein the load cell is deployed for measuring a compression force in only the cradle spring.

According to a further feature of an embodiment of the present invention, the position sensor is a second optical sensor comprising an emitter and a receiver.

According to a further feature of an embodiment of the present invention, the second optical sensor is configured to generate the second output indicative of the current position of the sliding cover based on an intensity of reflected light.

According to a further feature of an embodiment of the present invention, the position sensor is an electrical sensor generating the second output as a function of a variation in capacitance or inductance between two electrical components with variable overlap.

According to a further feature of an embodiment of the present invention, there is also provided a microswitch deployed relative to the sliding cover so as to be operated on engagement of the apparatus with the liquid delivery system, at least part of the apparatus having a low-power sleep state and being selectively activated on operation of the microswitch.

According to a further feature of an embodiment of the present invention, there is also provided a non-volatile data storage component associated with the processing system, and wherein the processing system is configured to store a previous location of the plunger, compare a current location of the plunger to the previous location, determine whether liquid has been dispensed, and to calculate a quantity of the liquid that has been dispensed.

According to a further feature of an embodiment of the present invention, there is also provided a display integrated with the sliding cover, wherein the processing system is further configured to display data relating to a delivered dosage.

According to a further feature of an embodiment of the present invention, there is also provided a wireless communication subsystem associated with the processing system and configured for transmitting data to an external device.

According to a further feature of an embodiment of the present invention, there is also provided a pen injector configured for delivering measured doses of a liquid drug via a needle, wherein the sliding cover is implemented as a cap with a central bore for receiving an end portion of the pen injector including the needle.

There is also provided according to the teachings of an embodiment of the present invention, an apparatus for use with a liquid delivery system, the liquid delivery system including a transparent cylinder for housing the liquid and a plunger movable along an axis of the cylinder for expelling the liquid through an outlet, the apparatus comprising: (a) a sliding cover configured for sliding engagement with the cylinder so as to be slidable along the cylinder parallel to the axis from a first position to a second position; (b) a set of sensors housed in the sliding cover so as to move together with the sliding cover, the set of sensors comprising at least a first sensor and a second sensor, the first sensor being a plunger sensor generating a signal, the plunger sensor being configured for non-contact sensing of at least part of the plunger as the sliding cover slides in engagement with the transparent cylinder such that variations in the first signal are indicative of the plunger passing a defined location along the sliding cover; and (c) a processing system associated with the set of sensors so as to receive outputs of the sensors, the processing system being configured to identify a variation in an output of the plunger sensor when the plunger passes the plunger, the processing system being further configured to process the outputs to derive a location of the plunger along the cylinder.

According to a further feature of an embodiment of the present invention, the second sensor is a position sensor deployed for generating a second output indicative of a current position of the sliding cover between the first position and the second position.

According to a further feature of an embodiment of the present invention, the first and second sensors are a pair of similar sensors spaced apart along the axis.

There is also provided according to the teachings of an embodiment of the present invention, a method for measuring the location of a plunger within a transparent cylinder of a drug delivery device for calculation of drug delivery dosing, the method comprising the steps of: (a) providing a sliding cover configured for sliding engagement with the cylinder so as to be slidable along the cylinder parallel to an axis of the axis from a first position to a second position, the sliding cover being provided with a plunger sensor configured for non-contact sensing of at least part of the plunger; (b) sliding the cover along the cylinder and sensing a variation in the first output corresponding to the plunger sensor reaching the plunger; and (c) employing at least one additional sensor output to determine a position of the cover relative to the cylinder when the plunger sensor reaches the plunger, thereby determining a position of the plunger.

According to a further feature of an embodiment of the present invention, the at least one additional sensor is a distance sensor deployed for measuring an axial distance between a part of the sliding cover and a part of the drug delivery device.

According to a further feature of an embodiment of the present invention, the plunger sensor is an optical sensor having an optical emitter for emitting radiation and an optical receiver for generating a first output indicative of an amount of the radiation received by the optical receiver.

According to a further feature of an embodiment of the present invention, the at least one additional sensor is a second optical sensor comprising an optical emitter for emitting radiation and an optical receiver for receiving the radiation, the second optical sensor being axially spaced from the first optical sensor, the method further comprising: (a) sensing a variation in the an output of the second optical sensor corresponding to the second optical sensor reaching the plunger; and (b) deriving from a time difference between features in outputs from the two optical sensors a speed of the sliding motion, the derived speed being used to determine a position of the plunger.

BRIEF DESCRIPTION OF THE DRAWINGS

The invention is herein described, by way of example only, with reference to the accompanying drawings, wherein:

FIGS. 2A-2C are schematic isometric views of the cap and pen injector of FIG. 1 with the pen injector outside, partially inserted, and fully inserted into the cap, respectively;

FIGS. 3A and 3B are schematic cross-sectional views taken through FIGS. 2B and 2C, respectively, along a central axis of the cap;

FIG. 4A is a schematic transverse cross-sectional view of an exemplary form of a pen injector reservoir;

FIGS. 4B and 4C are transverse cross-sectional views taken through an optical sensor of FIG. 3A illustrating insertion of the pen injector reservoir of FIG. 4A in two different orientations;

FIGS. 5A-5D are schematic side views of an exemplary pen injector showing a plunger in four sequential positions;

FIGS. 7A and 7B are views similar to FIGS. 3A and 3B, respectively, illustrating an implementation with an additional optical sensor;

FIGS. 8A and 8B are views similar to FIGS. 3A and 3B showing a variant implementation of a position sensor;

FIGS. 9A-9E are schematic axial cross-sectional views illustrating the principles of operation of a further variant embodiment of the present invention, shown in successive positions during uncapping of a pen injector;

DESCRIPTION OF THE PREFERRED EMBODIMENTS

Figure 1:
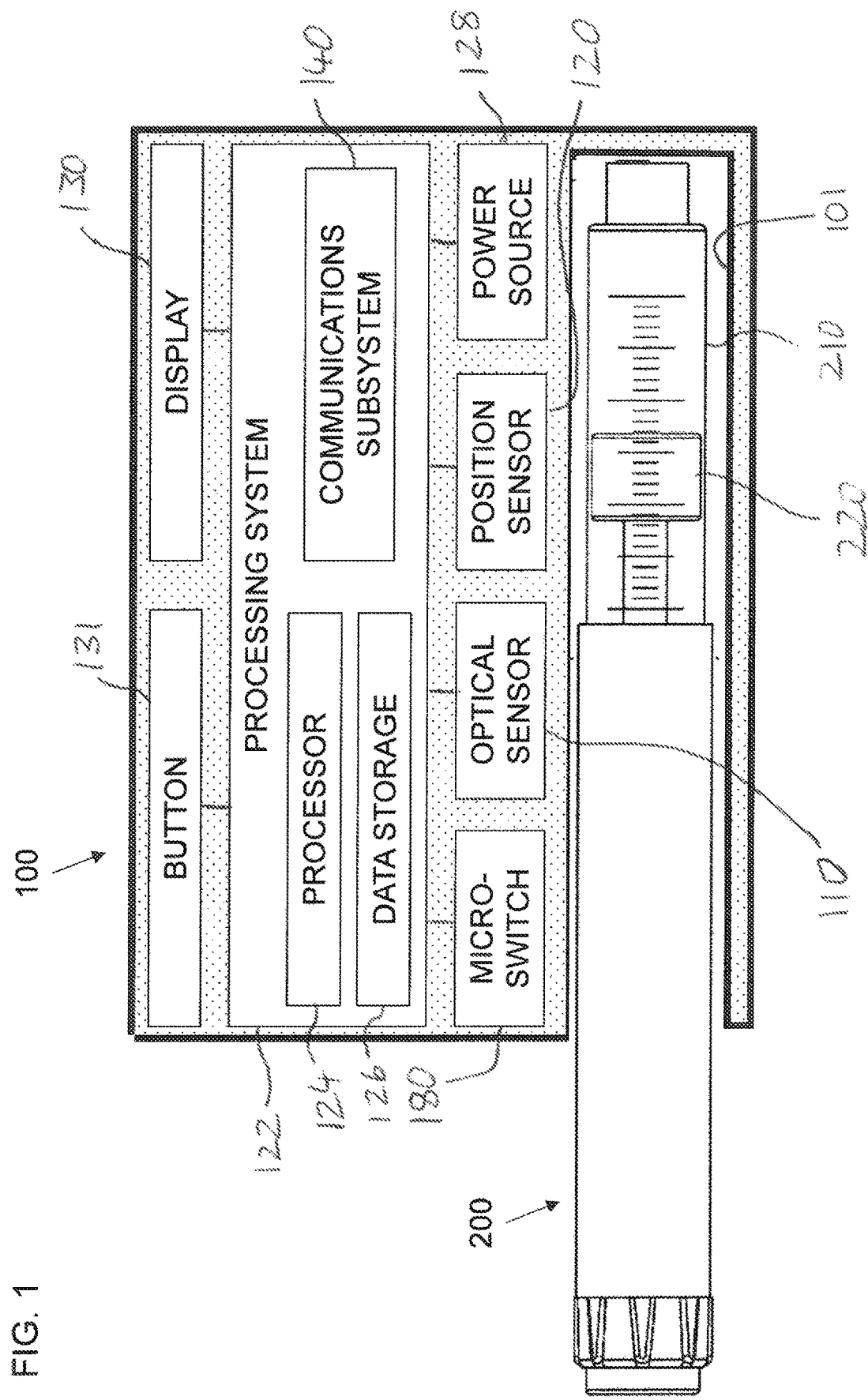
FIG. 1 is a schematic representation of a cap, constructed and operative according to an embodiment of the present invention, in use for capping a pen injector.
Figure 3C:
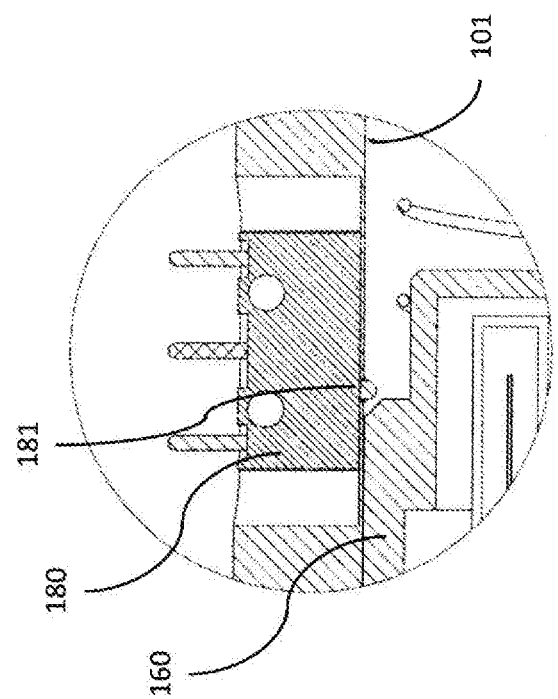
FIG. 3C is an enlarged view of a region of FIG. 3A designated III.

The present invention is an apparatus and corresponding method in which sensors are integrated with a sliding cover of a liquid delivery system, and measure the position of a plunger of the liquid delivery system while the cover is being removed or replaced.

The principles and operation of an apparatus according to the present invention may be better understood with reference to the drawings and the accompanying description.

By way of introduction, in general terms, the present invention employs a sliding cover, such as a cap for a pen injector, which incorporates a set of sensors including a first optical sensor which operates during an un-capping and/or capping motion of the cap to generate a signal which changes as the optical sensor reaches a plunger of the liquid delivery device. This signal is then used together with an output of at least one additional sensor to determine the position of the plunger along a cylinder of the liquid delivery device. By monitoring changes in the plunger position, the quantity of dosages delivered by the liquid delivery device can be determined, displayed, stored and/or transmitted to an external device for further data processing or storage.

Implementations of the present invention can be broadly subdivided into two subgroups, which both share a common inventive concept. A first subgroup, described herein with reference to FIGS. 1-8B, employs a position sensor together with the first optical sensor to measure a relative position of the liquid delivery device to the cover when the first optical sensor reaches the plunger. A second subgroup of implementations, exemplified with reference to FIGS. 9A-10D, employs at least one additional optical sensor to allow determination of a speed of movement of the cover relative to the liquid delivery device, and thus to derive the position at which the plunger is encountered.

Referring now to the drawings, FIGS. 1-7B illustrate features of a first apparatus, generally designated 100, constructed and operative according to an embodiment of the present invention, as a cap for an injection pen ("pen injector") 200, where pen injector 200 has a generally transparent reservoir in the form of a cylinder 210 with a transparent wall 211 for housing a liquid, and an at least partially opaque plunger 220 (interchangeably referred to herein as "piston" 220) movable along an axis of cylinder 210 for expelling the liquid through an outlet, typically implemented as a septum associated with an interchangeable injection needle 230.

Apparatus 100 is formed as a sliding cover, here a cap 100, configured for sliding engagement with cylinder 210 so as to be slidable along the cylinder parallel to the axis from a first position (FIGS. 2B and 3A), at the beginning of recapping, to a second position (FIGS. 2C and 3B) in which the cap is fully engaged with pen injector 200.

A set of sensors is housed in the sliding cover so as to move together with the sliding cover. The set of sensors includes an optical sensor 110 having an optical emitter 111 for emitting radiation and an optical receiver 112 for generating a first output indicative of an amount of the radiation received by the optical receiver. Optical sensor 110 is deployed in inward-facing deployment such that, when the sliding cover slides in engagement with transparent cylinder 210, the first output changes as optical sensor 110 passes plunger 220.

Also included in the set of sensors is a position sensor 120 deployed for generating a second output indicative of a current position of sliding cover 100 between the first position and the second position relative to pen injector 200. A processing system 122, including at least one processor 124, is associated with the set of sensors so as to receive the sensor outputs. Processing system 122 is configured to be responsive to a variation in the output from optical sensor 110 indicative of the optical sensor reaching plunger 220 to determine a corresponding current position of cover 100 as indicated by the output of position sensor 120, and thereby to determine a location of plunger 220 along cylinder 210.

Thus, certain embodiments of the present invention a provide distinctive mode of operation according to which detection of the plunger position is achieved using a sensor which is in sliding motion along cylinder 210. By harnessing the relative movement between the cover and the reservoir in the measurement process, precise measurements can preferably be achieved with a small number of sensors.

Turning now to the features of an embodiment of the present invention in more detail, optical sensor 110 is typically implemented as an emitter/receiver pair 111, 112, facing so as to interact with the liquid delivery device during sliding motion of the cover. In the preferred example of a cap with a central bore 101 for receiving an end portion of a pen injector, sensor 110 is typically implemented as a transmission sensor in which emitter 111 and receiver 112 are in facing relation across the central bore, most typically roughly along a diameter, so that the intensity of received light is affected by the part of the pen injector inserted between the two elements. In order to maximize measurement precision, in certain particularly preferred embodiments, emitter 111 is configured to generate a narrow beam with minimal spread in a direction parallel to the axis. This may be achieved by suitable choice of light source, such as a directional LED or laser diode, and/or by use of a collimating slit aligned perpendicular to the axis of the bore. Some degree of spreading within a plane perpendicular to the bore axis may be advantageous, although typically not necessary. The light source may operate at any desired wavelength of visible or invisible light. In various embodiments discussed below in which more than one optical sensor is used, cross-talk between the sensors may be avoided either by use of distinct wavelengths for each sensor (with receivers also rendered wavelength-specific, for example, by addition of a bandpass filter), or by time-division multiplexing in which each sensor emits and senses pulses of illumination in distinct time periods of a cycle. Sampling rates are preferably at least 100 Hz, and typically in excess of 1000 Hz.

In the case of a pen injector with a transparent cylindrical reservoir without optical obstructions, optical sensor 110 can essentially be implemented as a single emitter/receiver pair 111, 112. In certain cases, however, commercially available pen injectors have various structural supporting and/or protecting structures which partially obscure surfaces of the transparent cylinder. Thus, certain corresponding preferred implementations of the present invention provide solutions for addressing such obstructions, as will now be discussed.

FIG. 4A is a schematic cross-sectional view taken through cylinder 210 in which two opposing regions of cylinder wall 211 are overlaid by a plastic supporting structure 212 extending along the cylinder parallel to its axis. In this case, a single emitter/receiver pair optical sensor would be at risk of failing to sense the plunger, depending on the orientation in which the pen injector is inserted into the cap. According to one option (not shown), features formed in cap 100 complementary to asymmetric supporting structure features of pen injector 200 may ensure orientation of the cap relative to the pen injector in one of the orientations in which the emitter/receiver pair are aligned with the exposed regions of transparent wall 211, without being obscured by supporting structure 212.

According to an alternative optional solution, optical sensor 110 is implemented as illustrated in FIGS. 4B and 4C, with two or more optical emitters 111 spaced around the central bore and a corresponding plurality of optical receivers 112 spaced around the central bore. As a result, no matter what orientation the pen injector is inserted into the cap, at least one pair of optical emitter and optical receiver are unobstructed. Thus, for example, FIG. 4B illustrates a case where an emitter/receiver in the left-to-right direction as shown is obstructed by supporting structures 212 but the top-to-bottom emitter/receiver pair are operating, while FIG. 4C illustrates an orientation of the pen injector in which the reverse is true.

In this case, the multiple pairs of emitters/receivers are preferably located at a single axial position along the central bore, and are treated as a single sensor used to generate a single output. According to one particularly preferred option, the single output is generated through a preprocessing step performed by processing system 122 according to which the emitter/receiver pair with the largest dynamic range in its output is selected as the "active" part of the sensor, and the smaller-dynamic-range pair(s) is ignored. Other options, such as summing the outputs of the sensors, may also provide effective results, but are believed to afford less sensitivity than the selective use of the highest-dynamic-range output.

In certain commercially available pen injectors, there exist a further type of optical obstruction, as illustrated in FIGS. 5A-5D. In this case, in addition to the longitudinal supporting structures 212, pen injector 200 also features a number of bridging ribs 213 subdividing the window to the reservoir so as to form a number of fixed optical obstructions spaced along the transparent cylinder. The position of a leading surface 221 of plunger 220 can be optically sensed when it is opposite a "window" between ribs 213, as shown in FIGS. 5A, 5B and 5D, but in certain positions, such as in FIG. 5C, the leading surface 221 is obscured from view by one or other of ribs 213.

According to one aspect of an embodiment of the present invention, continuity of plunger position measurement is achieved in such cases by switching between sensing of the leading/front surface 221 and the trailing/rear surface 222 of the plunger. Specifically, processing system 122 is in this case configured to process the output of optical sensor 110 to detect variations indicative of optical sensor 110 passing both a front edge of the plunger and a rear edge of the plunger. (The leading and trailing surfaces as viewed from the side are observed as "edges".) During initial operation, processor 122 determines a location of front edge 221 of plunger 22 along the cylinder. When processor 122 determines that front edge 221 is approaching one of the fixed optical obstructions 213, the processor switches to determining a location of the plunger based on detection of rear edge 222 of the plunger. Given that the plunger has a constant known length (which can also be determined during measurements while both sides of the plunger are exposed, such as in FIG. 5B), the position of the leading surface 221 can thus be accurately determined even while it is obscured from view. Once the front edge 221 emerges from behind the obstruction, such as in FIG. 5D, processing system 122 typically switches back to determining directly the location of the front surface of the plunger. Optionally, where locations of both the front and rear edges of the plunger are detected, both measurements may be used to improve precision and/or for error checking. Whenever the position of either the front or the back edge is in proximity to an obstruction, the processing system switches to the use of the unobstructed edge only.

FIGS. 6A-6D show a schematic representation of the illumination intensity output I of optical sensor 110 as a function of insertion distance d of pen injector 200 into cap 100, corresponding to the states of FIGS. 5A-5D, respectively. It will be noted that the exemplary signal is shown here for the relatively more complex case of FIGS. 5A-5D which includes optical obstructions in the form of ribs 213. The operation of the simpler cases, without such obstructions, will be clearly understood by analogy from these drawings and the accompanying description.

Figure 6A:
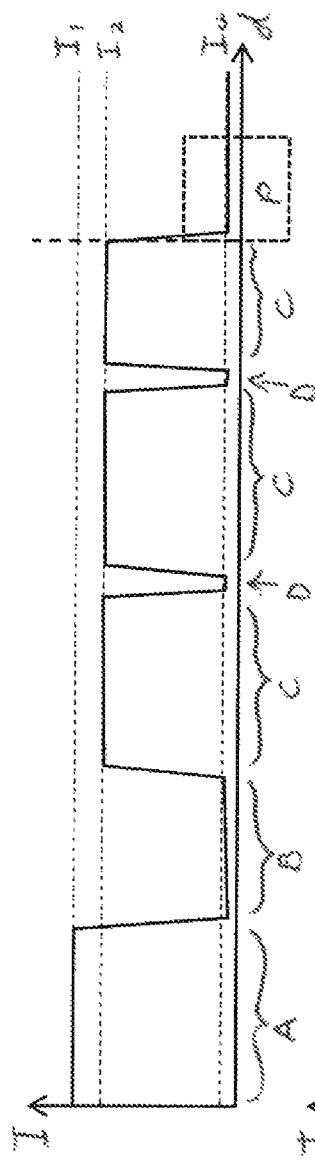
FIGS. 6A-6D are schematic graphs illustrating features of an output of the optical sensor of FIGS. 4B and 4C as a function of distance of insertion of the pen injector into the cap corresponding, respectively, to the plunger positions of FIGS. 5A-5D.
Figure 6B:
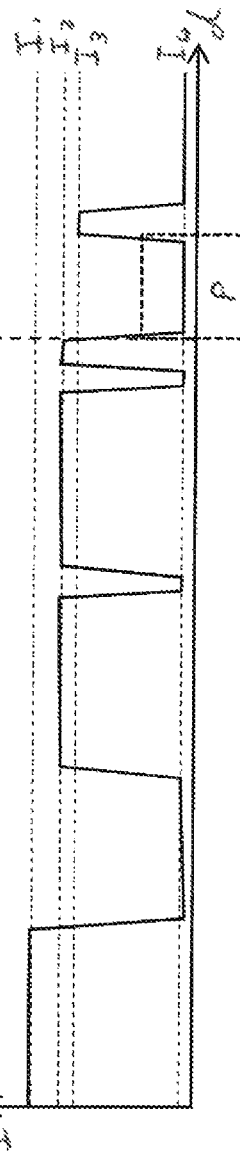
Figure 6C:
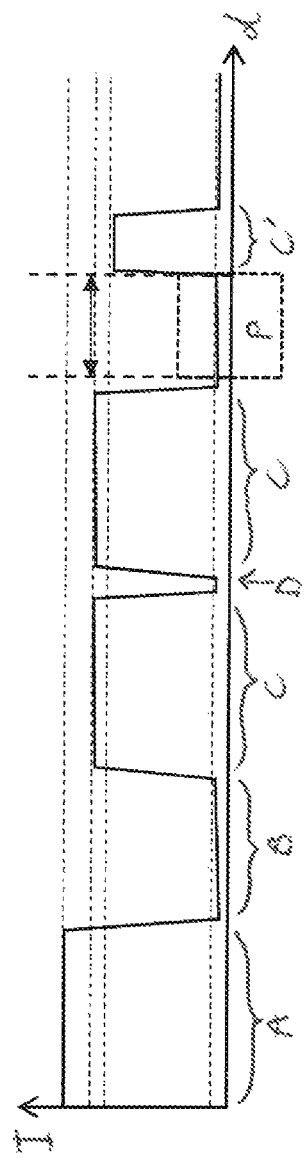
Figure 6D:
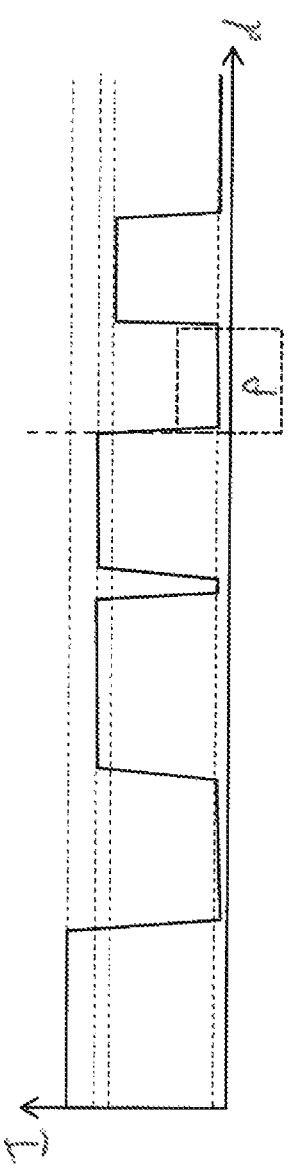

As designated in FIGS. 6A and 6C, the illustrated graph can be subdivided into regions corresponding to different parts of pen injector 200 which pass optical sensor 110. Thus, region A corresponds to the generally-unattenuated signal of level $I_1$ before the body of the pen injector has reached the sensor, but which might be slightly influenced by the presence of a projecting needle, in some cases, also with a needle cover 231 as shown. Where an internal sliding cradle 160 is used (as described below), this region just ahead of the pen injector is typically rendered opaque, and its optical properties are thus made independent of the presence/absence of the needle and cover, which further simplifies the detection process. Region B corresponds to the passing of the solid end-portion of the pen injector, which results in optical obstruction and correspondingly strong attenuation of the output signal to level $I_4$. As relative motion of pen injector 200 and cap 100 to increase overlap continues, at least one emitter/receiver pair of optical sensor 110 come into alignment with the window through cylinder 210, thus generating a relatively high signal at level $I_2$. Signal $I_2$ is typically slightly smaller than h due to scattering and/or absorption that occurs at the cylinder wall 211 and/or in the liquid. In this example, region C is interrupted by localized signal drops D caused by obstructions 213, after which the signal returns to level $I_2$ for a further part of window region C. Then when front edge 221 of plunger 220 reaches optical sensor 110, the signal again drops to $I_4$ until the entire plunger has passed (region P) or, in the case of FIGS. 5A and 6A, remains obscured through the remainder of the motion.

The location of the front (or back) edge of the plunger is preferably identified by the beginning of the gradient of the steep line for the corresponding change in signal, although other measuring points, such as the half-height of the signal, may also be used and render good results when used consistently.

FIG. 6C illustrates the signal corresponding to the state of FIG. 5C, where the front edge 221 cannot directly be found from the optical signal output, and the position is instead calculated based on measurement of the rear edge 222, as discussed above.

Although optical sensor 110 is exemplified herein with reference to a transmission mode, it should be noted that a reflective mode in which the emitter and receiver are deployed on the same side of the bore may also be used. The form of the resulting signals will be different, but all aspects of the processing described herein can readily be adapted in a manner that will be self-evident to one ordinarily skilled in the art.

In certain commercially available pen injectors, a position of the plunger during its initial stages of motion is recessed within an opaque region of the pen injector housing, and only reaches the exposed transparent part of the reservoir after a period of use. FIGS. 7A and 7B illustrate a modified version of cap 100 in which the set of sensors further includes a supplementary optical sensor having an optical emitter 113 for emitting radiation at an oblique angle through a wall 211 of the transparent cylinder towards a surface 221 of the plunger, and an optical receiver 114 for generating a supplementary output indicative of an amount of the obliquely angled radiation received by the optical receiver. In this case, plunger position is typically derived from intensity measurements, based on prior calibration for the given type of pen injector. Since this measurement modality is only used over a small range of positions at the beginning of the plunger range of motion, the measurements can be performed under static conditions, after complete insertion of the pen injector into the cap, and can typically achieve sufficient precision using a single supplementary sensor (optionally with multiple emitter/receiver pairs as discussed above with reference to FIGS. 4A-4C).

It should be noted that, in some cases, it may be possible to find wavelengths of illumination for the various optical sensors of the present invention which pass through various plastic parts of the device which are opaque to visible light. Thus, for example, it has been found that a beam of a solid state laser at 850 nm passes relatively unimpeded through the plastic support structures of various pen injectors, while be strongly attenuated by the silicone plunger of the devices. One non-limiting example of a suitable optical emitter for such a case is the vertical cavity surface emitting laser OPV382 commercially available from OPTEK Technology Inc. (US). The use of such wavelengths may obviate the need for some or all of the solutions described above with reference to FIGS. 4B-7B.

Turning now to additional features of certain preferred embodiments of the present invention, apparatus 100 may advantageously be provided with a sliding "cradle" 160 slidingly mounted within central bore 101, configured for receiving the end portion of pen injector 200. The term "cradle" as used here refers to a sliding block, also referred to herein as a "slider", which is shaped to receive the end portion of the pen injector, and preferably accommodates that end portion in a well-defined position independent of whether the pen injector currently has a needle adapter connected, with or without a needle cover, or is needleless with its septum interface exposed. This is preferably achieved by providing engagement features which engage the outer periphery of the front end of the reservoir, radially-outwards from the region of attachment of the needle adapter. Cradle 160 is preferably spring biased by a spring 170 towards an end position (FIG. 3A) for engaging the end portion of the pen injector when cap 100 is in a first position, at the beginning of recapping or the end of uncapping, and is retractable against spring 170 to move together with the end portion of pen injector 200 as cap 100 and pen injector 200 slide to a second fully-engaged position. The provision of cradle 160 helps to maintain precise alignment of pen injector 200 with cap 100 during motion, ensuring smooth and predictable motion of the pen injector within the cap, and thereby facilitating enhanced precision of measurement by optical sensor 110.

Turning now to position sensor 210, this may be implemented in many different ways, and using a wide range of different technologies, non-limiting examples of which will now be described. In some cases, the presence of cradle 160 may be used to advantage in implementation of the position sensor. For example, position sensor 120 may advantageously be associated with cradle 160 so that the output of the position sensor is indicative of a current position of cradle 160 within central bore 101. Since the engagement of cradle 160 with the end of pen injector 200 is well-defined, and since cradle 160 is spring-biased to maintain engagement with, and move together with, pen injector 200, position of cradle 160 can be used as a direct indication of the position of pen injector 200.

One particularly preferred non-limiting example of position sensor 120 illustrated in FIGS. 3A and 3B, employs a load-cell 171 deployed for measuring a compression force in spring 170. Since the compressive force on spring 170 is proportional to displacement of the spring according to Hooke's Law, measurement of the force on the load cell can be simply translated into a position of cradle 160, and hence of the pen injector 200. Processing system 122 is connected to load cell 171 so as to read an output of the load cell and translate that output into position of the pen injector. By processing the signal from optical sensor 110 to determine when the front (or rear) surface of the plunger is at a predefined location along bore 101, and by determining the corresponding position of pen injector 200 at that moment, the position of the plunger 220 within cylinder 210 can be derived. The difference between successive positions of the plunger together with a known cylinder internal diameter gives a calculated volume of a liquid dosage that has been delivered from the reservoir.

The use of a calculation based on Hooke's Law assumes that any dynamic effects occurring during motion of the spring are negligible. This assumption is typically a good assumption so long as the spring properties (primarily, mass and spring constant) are such that any internal oscillations of the spring occur at relatively high frequencies compared to the time over which the compression or extension of the spring occurs. If any oscillations are detected in the output signal that have a known characteristic frequency of the spring vibrations, these can be filtered out by processor 122.

The strength of spring 170 is preferably chosen in order to ensure that the load cell operates in its most sensitive range and/or in a range over which it provides a linear output response. In some cases this force may be greater than what is desired for the overall biasing force on cradle 160, leading to a risk of the pen injector being unintentionally ejected from the cap, or may be too small to reliably maintain engagement of cradle 160 with the tip of pen injector 200 during uncapping. In such cases, apparatus 100 may include a force adjustment spring (not shown), deployed within the cap, such that a biasing force acting on the cradle corresponds to a combination of the forces from the cradle spring 170 and from the force adjustment spring, while load cell 171 is deployed for measuring a compression force in only the cradle spring 170.

It is a particularly preferred feature of certain embodiments of the present invention that apparatus 100 is automatically actuated to take dosage readings once per dosing cycle, but assumes a low-power "sleep" state when not in use. A number of options may be used to achieve the automatic actuation. According to a first option, illustrated in FIG. 3C, mechanical switch, such as a microswitch 180 is provided to activate the device. The state of switch 180 is preferably changed when cradle 160 (moving with pen injector 200) passes over a switch button 181. Processing system 122 is responsive to the change of state of switch 180 to activate the device to its measuring mode, with all sensors actuated in their normal manner for measurement. The positioning of switch 180 as shown here is particularly suited to a system configured for performing measurements during a capping process, i.e., when the pen injector is inserted into the cap (or the cap is placed onto the pen injector, which is equivalent for the purposes of this application). In an alternative embodiment described below with reference to FIGS. 9A-10D, a microswitch is deployed at the distal end of cap 100 for actuating the system at the onset of an uncapping motion. In both cases, the device is preferably configured to return to a low-power sleep mode after a given time period sufficient to complete the capping or uncapping motion, which is typically not more than a few seconds. Optionally, subsets of components may be deactivated at different times, according to their functions, with the sensors being deactivated only sufficient time to complete the movement and associated measurements, while the processing and display components may remain active for longer to complete all necessary calculations and to display the results for a predefined period of time. A button 131 is typically provided to reactivate the display 130 on demand to display the most recent dosage data.

In an alternative implementation for achieving power-up from a sleep state without a mechanical microswitch, load cell 171 may itself be used in a low-power mode as an actuation sensor to sense the beginning of motion. In a typical case, a load cell is operated by an input voltage, and provides an output which is a variable proportion of the input voltage dependent on the current load. During normal operation, load cell 171 is provided with a working voltage which typically corresponds roughly to the input power supply voltage from power source 128, for example, 5V, to provide maximum resolution in the output signal. According to this feature of an aspect of the present invention, in a sleep mode, load cell 171 may be actuated by a reduced voltage, of less than 1V, such as for example 0.5V, and the output voltage is monitored by a low-power circuit which turns a small change in the output voltage into an actuation signal to processing system 122, which then reactivates all of the relevant components.

Referring briefly to the remaining components illustrated in FIG. 1, it will be appreciated that processing system 122 includes at least one processor 124 and a data storage device 126, preferably as well as communications subsystem 140. It will be appreciated that processing system 122 may be implemented in various ways, using standard processor chips suitably configured by software, or firmware, or by use of dedicated hardware, or any combination thereof, all in combination with suitable input and output interfaces required for driving and receiving outputs from the various sensors and other components of the system. Display 130 is typically a display of a limited number of digits or alphanumeric information, which typically displays the last delivered dosage and the time at which that dosage was delivered. For more extensive information, display of historical records and/or analysis of drug delivery patterns, data is preferably uploaded via communications subsystem 140, which may be a wireless communications subsystem according to any desired standard, such as Bluetooth, or a wired connection interface, such as a micro-USB connector, to an external electronic device. The external device may be a user device such as a personal computer (PC) or a mobile communications device (smartphone), or an Insulin pump and/or glucose monitoring device. The device may be running diabetic management software (e.g., an APP). Additionally or alternatively, the data may be transferred to a network-connected system of a healthcare provider. The may provide additional information, either directly or via an external device, including a history of the injections for a predetermined period of the time, and alert indications on empty cartridge, near empty cartridge, scheduled time for an injection, etc.

The entire apparatus is powered by a power source 128, which may typically be a number of miniature batteries, such as button-cells, which may be single-use or rechargeable cells.

It should be noted that the load cell-based position measurement described above is only one of a large number of possible technologies for implementing position sensor 120. A further example, illustrated in FIGS. 8A and 8B, implements position sensor 120 as an optical sensor employing an emitter 121 and a receiver 122 mounted within the closed end of bore 101 of cap 100, facing toward cradle 160. Most preferably, an end surface 161 of cradle 160 is implemented as a diffuse reflective surface, such as a white sheet of material. An intensity of illumination from emitter 121 reaching receiver 122 after reflection from end surface 161 provides an indication of the range of surface 161 from the end of bore 101. Since the cap is preferably a closed structure impenetrable to ambient light, relatively high precision of range measurement can be achieved using predefined look-up tables or a predefined formula, optionally intermittently self-recalibrated based upon one or both of the two known extreme resting positions of cradle 160.

Since pen injector 200 is engaged with cradle 160 in known spatial relation, the measurement of cradle position 160 yields also a measurement of position of the pen injector. As before, the measurement corresponding to the plunger reaching a predefined location along bore 101 is identified, and the position of the plunger along the reservoir cylinder is then determined. In all other respects, the structure and function of the apparatus of FIGS. 8A and 8B is structurally and functionally similar to the apparatus of FIGS. 2A-7B, with equivalent elements being labeled similarly, and will be understood by analogy thereto.

Position sensor 120 may alternatively be implemented using other optical sensor techniques including, but not limited to, triangulation techniques and time-of-flight ranging techniques, as are well known in the art of rangefinders.

In addition to the aforementioned implementations of position sensor 120, a range of other proximity-sensing and linear-encoder technologies may be used to implement one or both of the functions of sensor 110 (which may be more generally defined as a "plunger sensor") and position sensor 120. Other suitable sensing technologies for position sensor 120 include, but are not limited to: an electrical sensor generating an output as a function of a variation in capacitance (e.g., variable overlap of sliding conductors) or induction (e.g., sliding overlap of coils) between two electrical components with variable overlap; and ultrasound time-of-flight or intensity-based range sensor.

In cases in which the plunger 220 (itself or its rod) can be provided with a metallic implanted element, or the entire rod is implemented from metal, a linear variable differential transformer (LVDT) sensor can be used to replace optical sensor 110 to detect passing of plunger 220 at a predefined location along bore 101. If a further metallic reference element is incorporated near a front portion of the reservoir, an LVDT sensor can perform the functions of both sensors 110 and 120.

Turning now to FIGS. 9A-10D, there is illustrated a further implementation of apparatus 100 as a smart cap for a pen injector 200 in which direct measurement of position of the pen injector relative to the cap is replaced by a velocity-based calculation. Specifically, during the process of uncapping a pen injector, the user applies force greater than a required threshold force to overcome a positive engagement of the pen injector with the cap, which results in a rapid involuntary motion as the pen injector and cap move apart. This motion closely approximates to a uniform velocity motion over the relevant range of about 5 centimeters. This uniform velocity can be harnessed to perform measurement of the plunger position, as will now be described.

Referring to the schematic illustrations of FIGS. 9A-9E, apparatus 100 here includes a first optical sensor 110*a* located near a proximal end of internal bore 101, and a second optical sensor 110*b* located at some other location along bore 101. Each optical sensor is implemented according to any or all of the features described above in relation to sensor 110. The device also preferably includes a microswitch 180 deployed so as to be actuated (in this case, opened) by part of pen injector 200 when the pen injector is fully engaged with the cap, and to be switched (in this case, closed) by initial motion of pen injector 200 out of its fully engaged position (from FIG. 9A to FIG. 9B).

Optical sensor 110*b* is positioned so as to generate a variation in output as some optically-distinctive feature of pen injector passes it. In the case illustrated here, that feature is the distal end of the pen injector, which is detected as the position transitions from the state of FIG. 9B to that of FIG. 9C. This event is associated with a time $t_0$, or can be regarded as starting a timer.

Optical sensor 110*a* is deployed at a proximal location in apparatus 100 such that it generates a variation in output corresponding to passing of the plunger, as described above in detail in relation to sensor 110. This occurs as illustrated here in the transition between the states of FIGS. 9C and 9D, and is designated with a time $t_1$. As moving apart of apparatus 100 and pen injector 200 continues, the optically-distinctive feature seen by sensor 110*b* also passes sensor 110*a*, as illustrated in FIG. 9E, which is designated with a time $t_2$.

Processor 122 processes these outputs to derive the aforementioned times, and then determines the position of the plunger. A velocity of relative motion of the cap and the pen injector can be defined based on the distance L between the two optical sensors divided by $(t_2-t_0)$. The time $(t_2-t_1)$ multiplied by the velocity gives the distance between the plunger and the optically-distinctive feature of the pen injector.

Figure 10A:
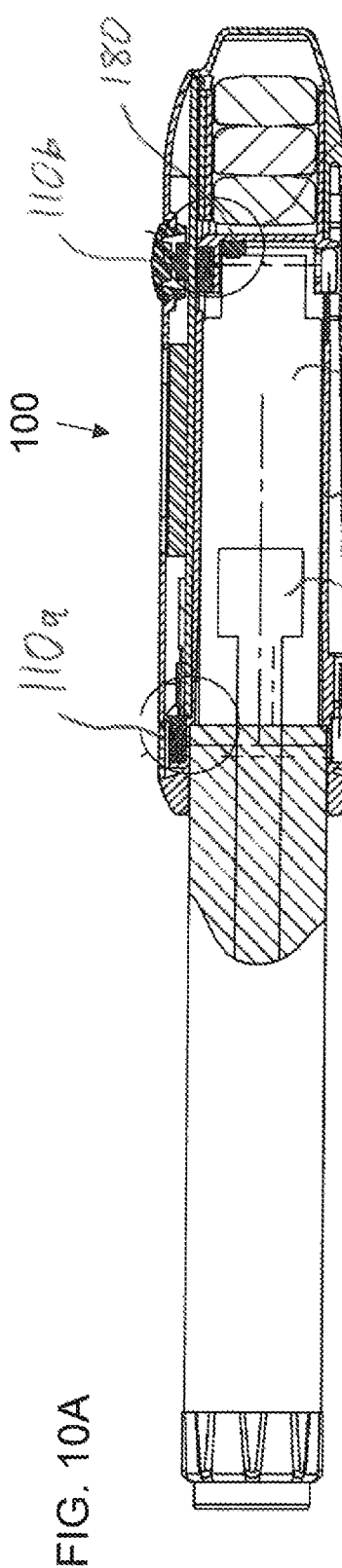
FIG. 10A is a schematic axial cross-sectional view illustrating in more detail an implementation of the present invention according to the principles of FIGS. 9A-9E.
Figure 10B:
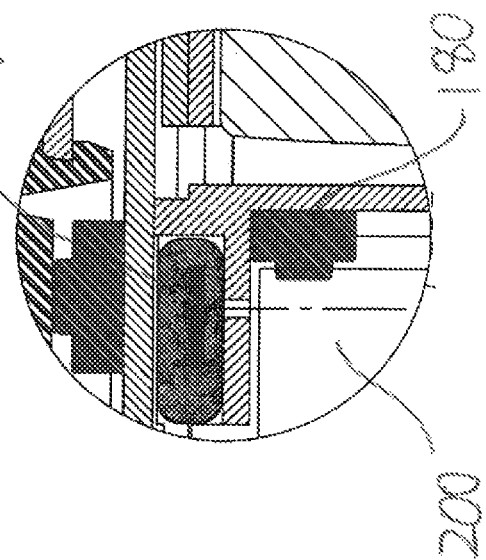
FIGS. 10B-10D are enlarged views of the region of FIG. 10A designated X, shown in states corresponding to the positions of FIGS. 9A-9C, respectively.
Figure 10C:
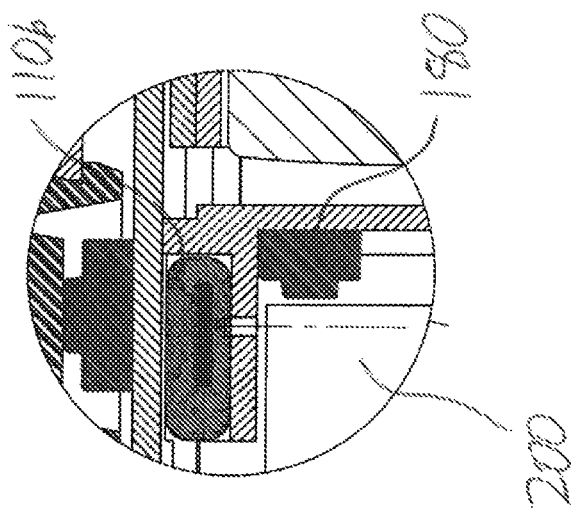
Figure 10D:
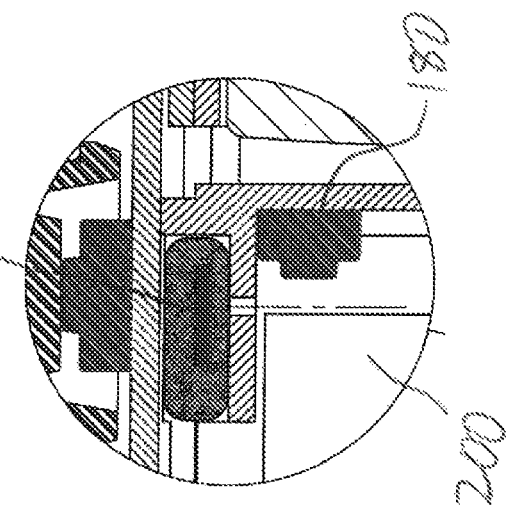

FIGS. 10A-10D illustrate in more detail a structure implementing the principles described with reference to FIGS. 9A-9E, showing deployment of microswitch 180 and the emitter of optical sensor 110*b*. FIGS. 10B-10D illustrate successive positions corresponding to the states of FIGS. 9A-9C, respectively.

In certain cases, where it is desirable to leave space for a user to recap the pen injector either with or without an attached needle and needle cover, microswitch 180 and optical sensor 110*b*, may advantageously be relocated to cooperate with regions of the pen injector which are not affected by the presence or absence of a needle adapter and/or cover, as will be clear to a person having ordinary skill in the art.

As mentioned in the context of the previous embodiments, in the event that suitable conductive (metal) components are incorporated into the pen injector construction, both in the plunger/rod assembly and at a distal region of the pen injector, an implementation of the invention functionally equivalent to that of FIGS. 9A-10D may be implemented using coil arrangement corresponding to two spaced-apart linear variable differential transformer (LVDT) sensors to determine $t_0$, $t_1$ and $t_2$.

At this stage, the operation of the various embodiments of the present invention, and a corresponding method according to the present invention, will be clear. Specifically, the various implementations detect the plunger position based on signals sampled during relative motion while the pen injector is being uncapped or recapped. The current plunger position is compared to the previously measured plunger position to determine whether a dose of drug has been administered and, if so, what dosage quantity. The cap then generates a display, typically on display panel 130, which indicates the time and quantity of the last dose delivered.

Although the present invention has been exemplified in the context of a pen injector, variant implementations of the present invention may be used to determine dosage delivered and/or remaining quantity in any context in which a drug or other liquid is delivered by a syringe-type device.

It will be appreciated that the above descriptions are intended only to serve as examples, and that many other embodiments are possible within the scope of the present invention as defined in the appended claims.

What is claimed is:

1. An apparatus for use with a liquid delivery system, the liquid delivery system including a transparent cylinder for housing the liquid and a plunger movable along an axis of the cylinder for expelling the liquid through an outlet, the apparatus comprising:

a sliding cover configured for sliding engagement with the cylinder so as to be slidable along the cylinder parallel to the axis from a first position to a second position;

a set of sensors housed in said sliding cover so as to move together with said sliding cover, said set of sensors comprising:

a plunger sensor generating a plunger signal, said plunger sensor being configured for non-contact sensing of at least part of the plunger as said sliding cover slides in engagement with the transparent cylinder such that variations in said plunger signal are indicative of the plunger sensor reaching the plunger, and a position sensor deployed for generating a position sensor output, wherein the position sensor is configured to generate the position sensor output indicative of a current position of said sliding cover between said first position and said second position; and a processing system associated with said set of sensors so as to receive outputs of said sensors including a plunger sensor output from the plunger sensor and the position sensor output, said processing system being configured to identify a variation in the plunger sensor output when said plunger signal indicates that the plunger sensor has reached the plunger, said processing system being further configured to process said position sensor output when the plunger signal indicates that the plunger sensor has reached the plunger to derive a location of the plunger along the cylinder.

2. The apparatus of claim 1, wherein the plunger sensor is an optical sensor having an optical emitter for emitting radiation and an optical receiver for generating the plunger sensor output indicative of an amount of said radiation received by said optical receiver, said optical sensor being deployed in inward-facing deployment such that, when said sliding cover slides in engagement with the transparent cylinder, said plunger sensor output changes as said optical sensor passes the plunger.

3. The apparatus of claim 2, wherein said sliding cover is implemented as a cap with a central bore for receiving an end portion of a pen injector having a projecting needle, and wherein said optical sensor is implemented using a plurality of said optical emitters spaced around said central bore and a corresponding plurality of optical receivers spaced around said central bore, such that, when used with a pen injector having optical obstructions extending along the transparent cylinder parallel to the axis, at least one pair of optical emitter and optical receiver are unobstructed.

4. The apparatus of claim 3, for use with a pen injector having a number of fixed optical obstructions spaced along the transparent cylinder, wherein said processing system is configured:

(a) to process said plunger sensor output to detect variations indicative of said first optical sensor passing a front edge of the plunger and a rear edge of the plunger;

(b) to determine a location of the front edge of the plunger along the cylinder; and (c) on detecting that a front edge of the plunger is approaching a fixed optical obstruction, to determine a location of the rear edge of the plunger.

5. The apparatus of claim 3, for use with a pen injector having an initial plunger position recessed within an opaque housing, wherein said set of sensors further comprises a supplementary optical sensor having an optical emitter for emitting radiation at an oblique angle through a wall of the transparent cylinder towards a surface of the plunger and an optical receiver for generating a supplementary output indicative of an amount of said obliquely angled radiation received by said optical receiver.

6. The apparatus of claim 3, further comprising a cradle slidingly mounted within said central bore, said cradle configured for receiving the end portion of the pen injector, said cradle being spring biased towards an end position for engaging the end portion of the pen injector when said sliding cover is in said first position, and being retractable to move together with the end portion of the pen injector as said sliding cover slides to said second position.

7. The apparatus of claim 6, wherein said position sensor is associated with said cradle so that said position sensor output is indicative of a current position of said cradle within said central bore.

8. The apparatus of claim 1, wherein said position sensor is a second optical sensor comprising an emitter and a receiver.

9. The apparatus of claim 8, wherein said second optical sensor is configured to generate said position sensor output indicative of the current position of said sliding cover based on an intensity of reflected light.

10. The apparatus of claim 1, wherein said position sensor is an electrical sensor generating said position sensor output as a function of a variation in capacitance or inductance between two electrical components with variable overlap.

11. The apparatus of claim 1, further comprising a microswitch deployed relative to said sliding cover so as to be operated on engagement of the apparatus with the liquid delivery system, at least part of the apparatus having a low-power sleep state and being selectively activated on operation of said microswitch.

12. The apparatus of claim 1, further comprising a non-volatile data storage component associated with said processing system, and wherein said processing system is configured to store a previous location of the plunger, compare a current location of the plunger to the previous location, determine whether liquid has been dispensed, and to calculate a quantity of the liquid that has been dispensed.

13. The apparatus of claim 12, further comprising a display integrated with said sliding cover, wherein said processing system is further configured to display data relating to a delivered dosage.

14. The apparatus of claim 1, further comprising a wireless communication subsystem associated with said processing system and configured for transmitting data to an external device.

15. The apparatus of claim 1, further comprising a pen injector configured for delivering measured doses of a liquid drug via a needle, and wherein said sliding cover is implemented as a cap with a central bore for receiving an end portion of said pen injector including said needle.

16. The apparatus of claim 1, wherein the position sensor operates independently from the plunger sensor.

17. A method for measuring the location of a plunger within a transparent cylinder of a drug delivery device, the method comprising the steps of:

(a) providing a sliding cover configured for sliding engagement with the cylinder so as to be slidable along the cylinder parallel to an axis of the axis from a first position to a second position, the sliding cover being provided with a plunger sensor configured for non-contact sensing of at least part of the plunger and a position sensor configured to generate a position sensor output indicative of a current position of said sliding cover between said first position and said second position;

(b) sliding the sliding cover along the cylinder and sensing a variation in a plunger sensor output corresponding to the plunger sensor reaching the plunger; and (c) employing the position sensor output generated by the position sensor to determine a position of the sliding cover relative to the cylinder when the plunger sensor reaches the plunger, thereby determining a position of the plunger.

18. The method of claim 17, wherein the position sensor is a distance sensor deployed for measuring an axial distance between a part of the sliding cover and a part of the drug delivery device.

19. The method of claim 17, wherein the plunger sensor is an optical sensor having an optical emitter for emitting radiation and an optical receiver for generating a plunger sensor output indicative of an amount of the radiation received by the optical receiver.

20. The method of claim 19, wherein the position sensor is a second optical sensor comprising an optical emitter for emitting radiation and an optical receiver for receiving said radiation, the second optical sensor being axially spaced from the first optical sensor, the method further comprising:

(a) sensing a variation in an output of the second optical sensor corresponding to the second optical sensor reaching the plunger; and (b) deriving from a time difference between features in outputs from the two optical sensors a speed of the sliding motion, the derived speed being used to determine a position of the plunger.

21. The method of claim 17, wherein the position sensor operates independently from the plunger sensor.

22. An apparatus for use with a liquid delivery system, the liquid delivery system including a transparent cylinder for housing the liquid and a plunger movable along an axis of the cylinder for expelling the liquid through an outlet, the apparatus comprising:
a sliding cover configured for sliding engagement with the cylinder so as to be slidable along the cylinder parallel to the axis from a first position to a second position;
a set of sensors housed in said sliding cover so as to move together with said sliding cover, said set of sensors comprising:
a plunger sensor generating a plunger signal, said plunger sensor being configured for non-contact sensing of at least part of the plunger as said sliding cover slides in engagement with the transparent cylinder such that variations in said plunger signal are indicative of the plunger sensor reaching the plunger, and
a position sensor deployed for generating a position sensor output indicative of a current position of said sliding cover between said first position and said second position; and
a processing system associated with said set of sensors so as to receive outputs of said sensors including a plunger sensor output from the plunger sensor and the position sensor output, said processing system being configured to identify a variation in the plunger sensor output when said plunger signal indicates that the plunger sensor has reached the plunger, said processing system being further configured to process said position sensor output when the plunger signal indicates that the plunger sensor has reached the plunger to derive a location of the plunger along the cylinder,
wherein said sliding cover is implemented as a cap with a central bore for receiving an end portion of a pen injector having a projecting needle, and
wherein said optical sensor is implemented using a plurality of said optical emitters spaced around said central bore and a corresponding plurality of optical receivers spaced around said central bore, such that, when used with a pen injector having optical obstructions extending along the transparent cylinder parallel to the axis, at least one pair of optical emitter and optical receiver are unobstructed,
further comprising a cradle slidingly mounted within said central bore, said cradle configured for receiving the end portion of the pen injector, said cradle being spring biased towards an end position for engaging the end portion of the pen injector when said sliding cover is in said first position, and being retractable to move together with the end portion of the pen injector as said sliding cover slides to said second position.

23. The apparatus of claim 22, wherein said position sensor is associated with said cradle so that said position sensor output is indicative of a current position of said cradle within said central bore.

24. An apparatus for use with a liquid delivery system, the liquid delivery system including a transparent cylinder for housing the liquid and a plunger movable along an axis of the cylinder for expelling the liquid through an outlet, the apparatus comprising:
a sliding cover configured for sliding engagement with the cylinder so as to be slidable along the cylinder parallel to the axis from a first position to a second position;
a set of sensors housed in said sliding cover so as to move together with said sliding cover, said set of sensors comprising:
a plunger sensor generating a plunger signal, said plunger sensor being configured for non-contact sensing of at least part of the plunger as said sliding cover slides in engagement with the transparent cylinder such that variations in said plunger signal are indicative of the plunger sensor reaching the plunger, and
a position sensor deployed for generating a position sensor output indicative of a current position of said sliding cover between said first position and said second position; and
a processing system associated with said set of sensors so as to receive outputs of said sensors including a plunger sensor output from the plunger sensor and the position sensor output, said processing system being configured to identify a variation in the plunger sensor output when said plunger signal indicates that the plunger sensor has reached the plunger, said processing system being further configured to process said position sensor output when the plunger signal indicates that the plunger sensor has reached the plunger to derive a location of the plunger along the cylinder,
wherein the position sensor operates independently from the plunger sensor.

\* \* \* \* \*